United States Patent [19]

Maass et al.

[11] Patent Number: 4,553,545

[45] Date of Patent: Nov. 19, 1985

[54] DEVICE FOR APPLICATION IN BLOOD VESSELS OR OTHER DIFFICULTLY ACCESSIBLE LOCATIONS AND ITS USE

[75] Inventors: Dierk Maass, Zürich; Hans I. Wallstén, Denens, both of Switzerland

[73] Assignee: Medinvent S.A., Lausanne, Switzerland

[21] Appl. No.: 498,189

[22] PCT Filed: Sep. 15, 1982

[86] PCT No.: PCT/SE82/00283

§ 371 Date: May 5, 1983

§ 102(e) Date: May 5, 1983

[87] PCT Pub. No.: WO83/00997

PCT Pub. Date: Mar. 31, 1983

[30] Foreign Application Priority Data

Sep. 16, 1981 [SE] Sweden ................... 8105510
Apr. 30, 1982 [SE] Sweden ................... 8202740

[51] Int. Cl.⁴ ............... A61M 29/00; C21B 15/00
[52] U.S. Cl. ................... 128/341; 267/167; 267/170; 604/104
[58] Field of Search ........... 128/341, 345, 334 R; 604/104; 267/167, 170

[56] References Cited

U.S. PATENT DOCUMENTS

| | | | |
|---|---|---|---|
| 3,509,883 | 5/1970 | Dibelius | 604/104 |
| 3,868,956 | 3/1975 | Alfidi et al. | 128/345 |
| 3,993,078 | 11/1976 | Bergentz et al. | 128/334 |
| 4,130,904 | 12/1978 | Whalen | 128/334 R X |
| 4,503,569 | 3/1985 | Dotter | 128/334 R X |
| 4,512,338 | 4/1985 | Balko et al. | 128/341 X |

Primary Examiner—William H. Grieb
Attorney, Agent, or Firm—Burns, Doane, Swecker & Mathis

[57] ABSTRACT

Device comprising a helically shaped spiral spring and means for bringing the spring to expand from a first state of a certain diameter to a second state of larger diameter and vice versa, characterized thereby that said means are arranged to rotate the ends of the spring relative to each other with maintained length of the spring so that the transition from said first state to said second state takes place by reducing the number of spring turns within said length and the corresponding increase of the pitch of the spring, or to supply to a given length of the spring further spring material at at least one end of the said length of the spring so that the transition from said first state to said second state takes place independent of pitch and number of spring turns within the said length; and a method for transluminal implantation of an intravascular prosthesis using the said device.

19 Claims, 29 Drawing Figures

DEVICE FOR APPLICATION IN BLOOD VESSELS OR OTHER DIFFICULTLY ACCESSIBLE LOCATIONS AND ITS USE

TECHNICAL FIELD

The present invention relates to a device which can be applied within for example blood vessels of the body of a living animal or a living human being. The device comprises a helically shaped coil spring that can be expanded from a first state of a certain diameter to a second state of larger diameter and vice versa.

The invention is particularly useful for mechanical transluminal implantation by means of an expanding, self-fixating applicance for blood vessels, respiratory tracts or the like. By means of the device of the present invention also the inner walls of damaged blood vessels or other organs may be lined with artificial tissue which may be porous.

In surgical and other medicinal techniques there is sometimes a need of inserting and expanding a device in for example blood vessels, urinary tracts or other difficultly accessible places which has for its function to widen the said vessel or tract, the device being optionally left in position to provide for permanent widening.

The device according to the present invention may be used in many medicinal applications and, as examples, there may be mentioned utilization in different types of aneurism reflected by some form of vessel widening, or the opposite, stenosis, which involves contraction of blood vessels. More particularly, the invention thus may be used to support and keep open vessels of venous systems, to support artificial vessel elements, to close pathological vessel failures, to bridge pathological vessel dilatations and ruptures in interior vessel walls or to stabilize bronchial tubes or bronchi. The device of the present invention may also be designed to act as a filter for thromboses, for example by application in Vena Cava Inferior to prevent the formation of lung emboliae. However, the invention is not limited to the applications mentioned herein which must be considered as solely exemplifying.

BACKGROUND ART

In U.S. Pat. No. 3,868,956 there is described a device which after insertion into for example blood vessel may be expanded. The active part of this device is based on the use of metal alloys having so-called "memory function", i.e. a material which when heated will recover its initial configuration. In this prior art the heating of the material is provided by electrical heating, the device being inserted at the location of interest. However, this known technique possesses the essential disadvantage that electrical resistance heating must take place in connection to surrounding sensitive tissue which may be damaged in the heating. It is true that it is stated in the patent specification (cf.col.3, lines 42-48) that when inserting the device into a blood vessel the patient's blood functions as a cooling medium. However, also blood is a heat-sensitive material which when heated can be subjected to undesirable coagulation.

SUMMARY OF THE INVENTION

The present invention has for its purpose to provide for an expansible device whereby the drawbacks of the known technique are avoided.

The present invention is based on the utilization of a device comprising a helically shaped coil spring which can be subjected to contraction or expansion. The invention is based on the principle that the spring will be given smaller or larger diameter by means of suitable mechanical means. This is possible to do in two principally different ways which all fall within the framework of the same basic inventive concept. In the following there are given examples of two of these ways.

A first way consists in rotating the ends of the spring relative to each other while maintaining a constant length of the spring so that the transition from a smaller spring diameter to a larger one takes place by reducing the number of spring turns within said length and the corresponding increase of the pitch of the spring. A second way to change the diameter of the spring consists in removing part of the spring material from a given length of the spring at at least one end of the said length of the spring, so that the transition from a state of larger diameter to a state of smaller diameter takes place independent of pitch and number of spring turns within said length. In order to expand the spring in said other way the reverse operation is, of course, performed, i.e. additional spring material is supplied to the said length of the spring. This second way of changing the diameter of the spring may, if desirable, take place while maintaining pitch and number of spring turns within the said length.

Both said ways may, of course, be used to change the coil spring from a state of larger diameter to a smaller diameter and vice versa.

In a preferred embodiment of the device according to the invention the larger diameter corresponds largely to unloaded condition of the coil spring. This means that the contraction of the coil spring takes place against its spring resistance, whereas its expansion takes place under release of the tension to unloaded state.

While utilizing the above-outlined first way of contracting or expanding the spring one end of the spring may be attached to a shaft which is centrally arranged inside the spring, whereas its other end is connected to a sleeve surrounding said shaft. By turning the shaft and/or the sleeve relative to each other the diameter of the spring can hereby be decreased or increased. In order to make it possible to leave the coil spring also after application at a location the shaft and the sleeve can be removably connected to same.

When using coil springs of a minor dimension in regard to the spring material problem may arise in connection with applying the spring and expanding same at the intended location in that the separate material turns of the spring may fall to one side so that the desired supporting effect will not be obtained. In order to eliminate or reduce the risks for such spring collapse an axially extending guide bar can be arranged at the circumference of the spring, on which bar guide meanns are displaceably arranged through which the spring material can move tangentially in connection with the contraction or expansion of the spring.

In an alternative embodiment of the device according to the invention an axially extending support member can be arranged at the circumference of the spring which carries fixed guide means through which the spring material can move tangentially in connection with the expansion or contraction of the spring.

In certain instances, for example in case of hernia or tissue rupture, it may be desirable to apply a spring which over a limited part of its length has a larger density between the spring turns. This can in principle be done in two different ways. One alternative is based on distributing the above-mentioned fixed guide means in such a manner as to obtain over a certain length of the spring a larger density of turns. The second alternative consists in initially manufacturing the spring with one or several sections of higher turn density. Also a combination of these two alternatives may, of course, be used in practice.

It is to prefer, in view of the above-indicated risk for collapse, to make the spring material in a flattened form or in the form of a band, the larger dimension of the material as seen in cross section extending axially. It is particularly preferred to design the spring with an essentially rectangular cross section.

In a particularly preferred embodiment of the device of the present invention a cylindrical tubular carrier body is arranged within the coil spring comprising a central part and being provided with end sections at the ends of the spring pivotal relative to each other, the ends of the spring being connected to the respective end sections. The device furthermore includes means with the help of which the said end sections can be rotated relative to each other in order to expand or contract the spring. Said means for rotating the end sections suitably comprise a coaxial cable connected to the one end section, the interior concentric element of the cable extending through the carrier body and being at the end connected to the other end section, rotators being arranged at the outer free end of the coaxial cable for providing the desired relative movement between the end sections.

In connection with this latter embodiment of the device according to the invention the end sections of the carrier body may be axially displaceable relative to the central part so that in the gap between the central part and the respective end sections the end of the spring can be releasably attached. In this case it is suitable to arrange at least one end section or part thereof axially displaceable by means of a member arranged at the free end of the coaxial cable. The last-mentioned member may optionally perform the two-fold function of both to be used for rotating the second end section and providing for the axial displacement.

In a particularly preferred embodiment of the device according to the present invention there is arranged an axially extending support member at the circumference of the spring, at the one end of which the spring is attached and at the other end of which there is provided a fixed guide member through which the spring material can move in connection with the contraction or expansion of the spring.

Alternatively, at both ends of the support member there may be arranged fixed guide means, through which the material of the spring can move. This embodiment enables simultaneous feeding in both directions of spring material at both ends of the spring.

According to an alternative embodiment the device of the invention comprises an elongated carrier body about which the spring is arranged, a cassette magazine arranged at one end of the carrier body including a cylindric cassette housing, a feed cylinder eccentrically mounted therein which at its periphery engages the inside of the cassette housing. Using this device the spring can be moved for contraction or expansion in the nip between the cassette housing and the feed cylinder by rotating the latter in one direction or the other. In this embodiment the cassette housing may be provided on the inside with a trapezoid thread in which the spring can glide. Moreover, it is suitable to provide the feed cylinder on its exterior with a friction coating, for example of rubber or plastic.

In surgical operations for implanting prostheses it is sometimes desirable to provide for a porous tissue inside for example a blood vessel for some reason. In connection hereto it is possible in accordance with the invention to provide for a stocking of porous tissue outside or inside the spring which can be implanted at desired location together with the spring. The stocking may either by stretchability of the tissue or by overlapping folding be adjustable to the spring diameter in connection with the expansion of the spring.

In regard to the choice of material for the components involved in the device according to the invention it is primarily the coil spring which is critical in this respect. For the spring there should be selected a medicinally acceptable material, for example a stainless steel or other metal alloy or a plastic, used in similar connection.

Other characterizing features and alternative embodiments will be evident from the following description and the appended patent claims.

A further essential advantage of the technique of the present invention compared with for example that of the above-mentioned U.S. Pat. No. 3,868,956 lies in the fact that the device according to the invention is reversibly operable, i.e. the spring may first after application be expanded, whereafter before releasing the spring from the other members of the device one can check, for example by X-rays, that the position and fixation of the spring is acceptable, whereafter it can be released and the remaining part of the device removed from the location of application. This possibility is not at all available in the device according to the just mentioned U.S. patent, since the expansion initiated in this known technique is non-reversible.

EXAMPLES

The invention will in the following be further described by exemplifying embodiments in connection with the appended drawings. It should be noted that these specific embodiments are only intended to be illustrative and not restrictive in regard to the scope defined by the claims. In the drawing the following is illustrated:

FIG. 13A shows diagrammatically a spring provided with support member and a fixed guide member;

FIG. 13B shows a detail of the embodiment of FIG. 13A;

In connection with the following description it is assumed that the device according to the invention is utilized in connection with a blood vessel containing a defect location, where the blood vessel has relatively large diameter, whereas the location where the device is introduced into the blood vessel has a smaller diameter. However, the device according to the present invention may be used also in cases where it shall be inserted in a blood vessel of a relatively constant diameter thereby to avoid damages to the inner walls of the blood vessel in connection with inserting the device for transfer to the location where application shall take place.

Thus, the device according to the invention can be inserted at an easily accessible location where the blood vessel in question has a relatively small diameter due to the fact that the coil spring of the device can be maintained in contracted state by mechanical means, said state being small or smaller than the diameter of the blood vessel at the location of insertion. The device including the coil spring is then inserted into the blood vessel and transferred to the defective location where the coil spring in a mechanical manner is expanded until the outer diameter of the spring is equal to or somewhat larger than the diameter of the blood vessel at the defective location. Then the coil spring is suitably released from the other members of the device according to the invention and may after removal of the remaining part of the device thus be left at the defective location for carrying out its supporting function from the inside. If the diameter of the spring in unloaded state is selected somewhat larger than the inner diameter of the blood vessel the spring will fixedly engage the walls of the vessel by a certain specific pressure the magnitude of which can be precalculated and thus selected as desired.

Figure 1:
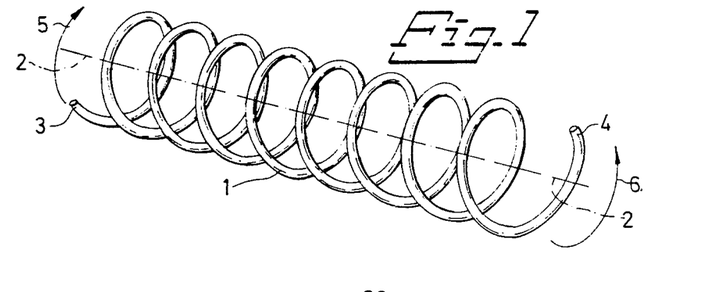
FIG. 1 shows a perspective view of a coil spring for use in the device according to the invention.
Figure 2:
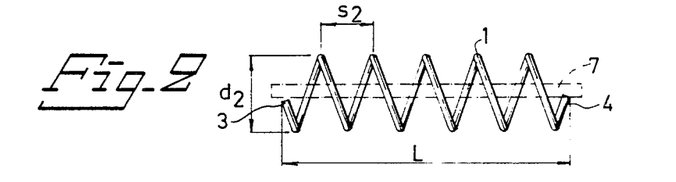
FIG. 2 shows a side view of the coil spring containing a carrier body and showing the spring in expanded state.
Figure 3:
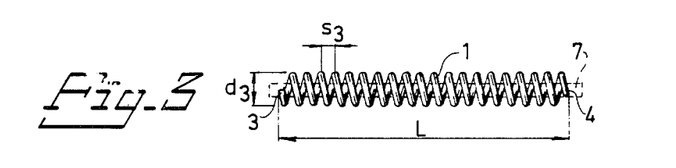
FIG. 3 shows the same device as FIG. 2 but showing the spring in contracted state.

In drawing FIGS. 1, 2 and 3 there is shown in principle how a helically shaped coil spring according to an embodiment of the invention can be subjected to change in diameter. FIG. 1 shows diagrammatically a coil spring having diagrammatically shown longitudinal axis 2. The ends of the spring are designated 3 and 4. The coil spring of FIG. 1 is assumed to be in a position of rest, i.e. it has taken the shape it has when not effected by external forces. If now the ends 3, 4 of the spring are rotated around the longitudinal axis 2 in the direction of arrows 5, 6 under the influence of an external force the spring diameter will decrease at the same time as the number of turns increase in a corresponding degree. In FIG. 2 there is shown a coil spring 1 in position of rest as seen in a side view. In FIG. 3 the same spring 1 is shown after reduction of the diameter has been provided for in accord with the description relative to FIG. 1. In its position in FIG. 3 spring 1 has been given a diameter d3 which is one third of the diameter d2 of FIG. 2, whereas the number of turns is three times as large as the number of turns in position of rest. Since the length L of the spring is maintained unchanged the pitch s3 of the helical spring in the position according to FIG. 3 is one third of the pitch s2 of the position of rest according to FIG. 2.

In FIGS. 2 and 3 there is shown with dashed lines a cylindric central body 7 having for a function to stabilize the spring 1 in its contracted condition acc. to FIG. 3.

Figure 4:
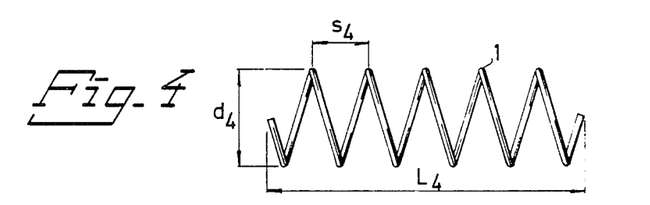
FIGS. 4-7 illustrate diagrammatically the principle of removing spring material from a coil spring in accordance with the invention.
Figure 5:
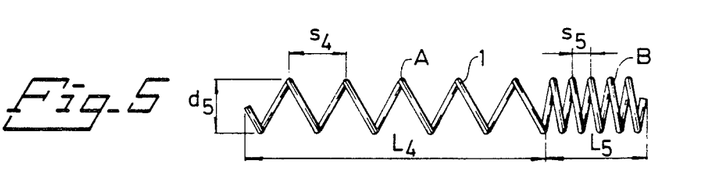
Figure 6:
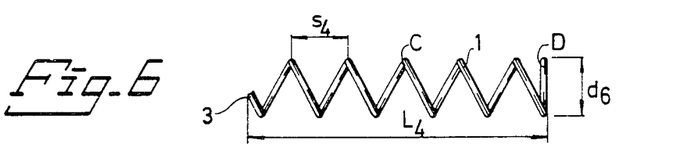

In FIGS. 4-7 there is shown the principle for another embodiment acc. to the invention, according to which the diameter change of the coil spring is provided without changing the pitch of the spring. A coil spring 1 is acc. to FIG. 4 in its position of rest with diameter d4, length L4 and pitch s4. In FIG. 5 the same spring is shown but having the diameter d5 reduced to about half of the diameter d4 according to FIG. 4. However, in this state the spring has two parts A and B of different pitch. Part A has the same length L4 and pitch s4 as the spring has in position of rest, whereas part B has a length L5 which is considerably smaller than L4 and a pitch s5 which is considerably smaller than s4. The reduction of the diameter from the position of rest according to FIG. 4 to the state according to FIG. 5 can be provided by rotating the ends of the spring in the same manner as shown in FIGS. 1-3. Dividing up the contracted spring in two zones of different pitches can thus be provided by means of suitable mechanical aids. In FIG. 6 there is shown the same spring 1 as in FIG. 4 but having a diameter d6 which has been reduced to about half of diameter d4. The spring has two parts C and D. Part C has the same length L4 and pitch s4 as the spring has in its position of rest. In part D spring 1 forms a concentric flat spiral spring.

Figures 7, 8, 9:
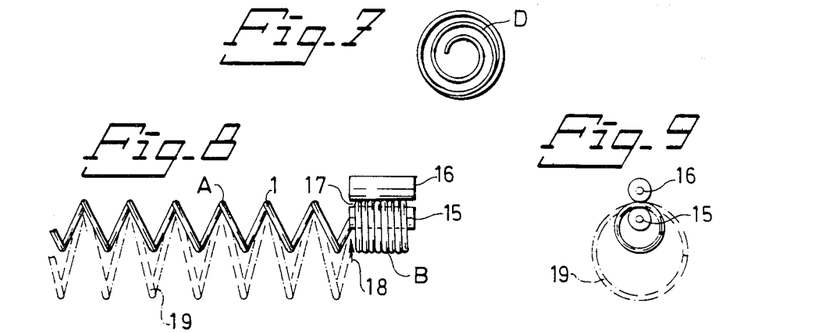
FIGS. 8 and 9 show a variant based on the same principle as that according to FIGS. 4-7.

In FIG. 7 there is shown the spiral spring acc. to FIG. 6 but in an end view, from which the appearance of part D is clear. In this embodiment the total length L4 of the spring and the pitch s4 is thus the same as in the position of rest of the spring. The change of spring 1 from position of rest to the state according to FIGS. 6 and 7 can be provided by using suitable mechanical devices.

In FIGS. 1-7 there has thus been shown how the diameter of helically shaped coil springs according to the invention can be changed to enable for example surgical operations. In the following there will be described some different practical solutions to provide for the desired expansion or contraction of the coil spring.

Part B of the embodiment according to FIG. 5 may also be considered as a storage part of the coil spring material from which in the expansion the part A of spring material is supplied. In FIGS. 8 and 9 there is shown a side view and an end view, respectively, of a device in which the just mentioned principle is applied. In the storage part B the spiral turns lie close to each other. FIGS. 8 and 9 show diagrammatically how the feeding can take place through a nip formed between two counter-rotating small feeding rollers 15 and 16, whereby spiral material is progressively and controlled fed out at the end 17 of the roller nip in the direction of arrow 18. The dashed line 19 in FIGS. 8 and 9 shows part A of the coil spring after expansion to position rest has taken place.

In connection with application of coil springs by means of the device according to the present invention it is, of course, possible after the application to change the length of the spring as required by manipulation from the outside for adaptation to different situations. Thus, the spring may before, during and after the expansion be axially compressed in order to then be axially extended to for example neutral unloaded state and even to an expanded state beyond neutral. This later case may result in certain further stabilization of the spring in view of tension stored therein.

When applying the technique according to the present invention for surgical operations in the human body the diameter of the coil spring in contracted or reduced state is suitably not larger than 8 to 10 mm. The diameter in expanded state may lie between 12 and 30 mm. An expansion such as for example from 8 mm to 12 mm, i.e. an expansion degree of 50% or an expansion number of 1.5 (12/8 = 1.5) is possible with for example a coil spring made of a thread of stainless steel having a thickness of about 0.3 mm. However, it has been found that by using this thread material it is not possible to manufacture a coil spring which in its position of rest in expanded state has a diameter of about 30 mm. Investigations have shown that for all spring materials of interest there is a relation between material thickness and expansion number. The relation is depending on the material but in general the higher the expansion number desired the thinner the thread material to be selected. As an example there may be mentioned that to make possible a position of rest at 30 mm diameter from a contracted state of 8 mm in diameter, i.e. an expansion number of 3.8 there will be required a steel band of stainless material having a width of 1 mm and a thickness of about 0.15 mm. Quite generally a suitable interval concerning thread or band thickness is about 0.08 to 0.30 mm. As regards the breadth of band material a suitable interval is about 0.3 to 2 mm. In other words this means that for utilizing the technique according to the present invention for surgical purposes in most cases one has to utilize a thin material in thread or band form for manufacturing the coil spring. However, a coil spring based on such material gives satisfactory support when applied in for example a defective blood vessel.

Figure 10:
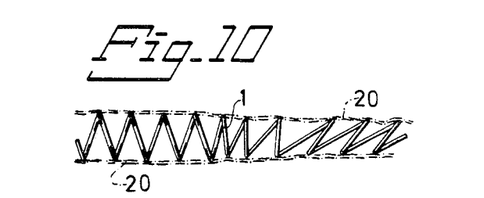
FIG. 10 shows diagrammatically the possible performance of the coil spring under the influence of external forces.

In practice it has been found that coil springs made of thin material have a tendency in expanded state to be mechanically instable. Thus, this results in tilting or collapse of the spring after its application. In FIG. 10 there is shown diagrammatically how a coil spring 1 made of a thin material can perform in view of instability in expanded position after it has been applied. The dashed line indicates the vessel wall of a blood vessel wherein the spring has been expanded. Such instability of the coil spring is often not acceptable, since the coil spring does not perform its intended function to eliminate the said defect but can rather act restricting on the flow of blood.

Figure 11:
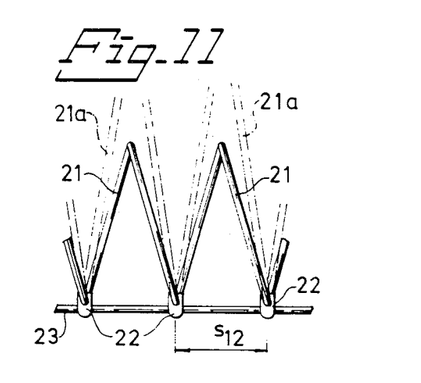
FIG. 11 shows a detail of the coil spring using guide means.
Figure 12:
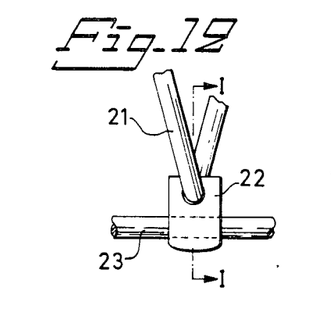
FIG. 12 shows in enlargement a detail of the device of FIG. 11.
Figure 13:
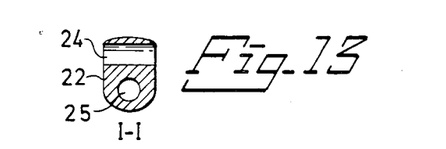
FIG. 13 shows a detail section along line I—I in FIG. 12.

According to the invention the risk for such spring collapse can be eliminated or at any rate essentially prevented by providing the coil spring with rigidifying devices active with the coil spring both in contracted and in expanded state. Drawing FIGS. 11, 12 and 13 illustrate an embodiment of the device according to the invention provided with such rigidifying means. FIG. 11 shows diagrammatically part of a coil spring which in contracted state is designated 21 and in expanded state is designated 21a. In the figure three guide member 22 for the coil spring are shown. Guide members 22 are arranged on a common flexible but relatively rigid thread 23 at a mutual distance of s12, as is clear from FIG. 11.

FIG. 12 shows a detail of the device of FIG. 11 in enlargement and FIG. 13 shows a section along line I—I in FIG. 12. As is clear from FIGS. 12 and 13 the coil spring 21 extends through a hole or a recess 24 in guide member 22, whereas thread 23 extends through the hole 25 of guide member 22.

In connection to the embodiment illustrated in FIGS. 5 and 6 it is suitable to arrange guide members 22 fixedly attached to thread 23. In this manner the pitch s12 will be maintained at contracted as well as expanded state, all in conformity with the earlier description in connection with drawing FIGS. 5 and 6.

FIG. 13A shows an embodiment of a coil spring in expanded state stabilized by means of a fixed guide member. Coil spring 21 which is suitably made of a thin metal band is as its end 21a fixedly attached to the axial support member 23a, suitably consisting of one flexible band or two flexible bands attached to each to each other. The other end 21b of the coil spring 21 is connected to support member 23a by means of a single fixed guide member 22a in the form of a loop having a rectangular opening. It has been surprisingly found that spring 21 in this embodiment is sufficiently stable for practical use and that it is sufficient that the end sections of the spring are stabilized and connected to each other by means of support member 23a. The advantage of this embodiment containing one single guide member is that the expansion or contraction of the spring is facilitated by the fact that the spring need to pass only through one single guide member.

FIG. 13B shows in enlargement a suitable design of guide member 22a and its connection to support member 23a. Guide member 22a is formed by using a band having a loop-like protrusion which, together with support member 23a, forms a rectangular recess 22a. In said recess spring band 21 may easily slide while stabilized at the same time.

Alternatively, the last described embodiment according to FIGS. 13A and 13B can be modified by arranging a fixed guide member at each end of support member 23a. In this manner spring band material can be fed into or fed out from both ends of spring 21 simultaneously which can be of advantage at large expansion numbers when larger lengths of spring band material have to be stored at both ends of the spring in connection with the contraction of the spring.

In connection to this embodiment even better stabilization of the spring in expanded state will be obtained if the distance between fixed points 21a, 22a is made longer than the normal length of the spring in neutral, un-loaded state.

In embodiments in accordance with FIGS. 2 and 3 guide members 22 are, however, displaceably arranged on thread 23, whereby the pitch of the coil spring can be changed in accordance with what has been earlier described.

Figure 14:
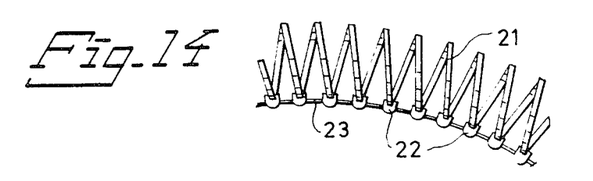
FIG. 14 shows diagrammatically a spring provided with support member and guide member.

FIG. 14 shows diagrammatically in a side view a coil spring thus stabilized in expanded rest position.

It has been previously indicated that the material of the coil spring suitably is in thread or band form, i.e. that the material of the coil spring in an axial cross section has a round or flattened shape. It has been found that coil springs made of band-formed material are more stable and have less tendency to tilt or collapse. As a rule, however, the band width should not exceed 1 to 1.5 mm for medicinal reasons. Larger width hampers the growth of tissue and results in inferior fixation in view of lower specific engagement pressure. High specific engagement pressure is to prefer since it gives a better fixation which is essential in applications in blood vessels, where the pulse rhythm can result in displacement of an applied spring in an axial direction. One way of improving fixation is to coarsen the outer surface of the spring material by for example blastering. The spring material may also by punching be provided with outwardly extending protrusions or, alternatively, the band material can be perforated, for example by punching or by using a laser, whereby better fixation will be obtained and the growth of tissue in the area where the spring has been applied is facilitated.

Figure 15:
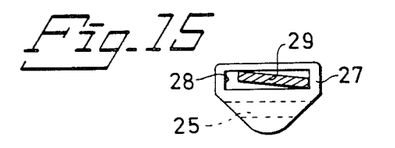
FIG. 15 shows a detail of an alternative guide member.
Figure 15A:
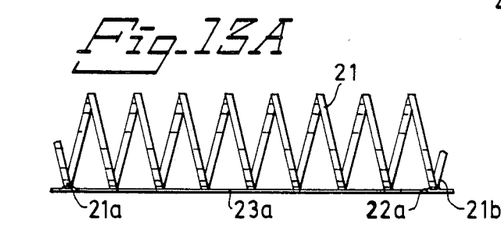
Figure 15B:
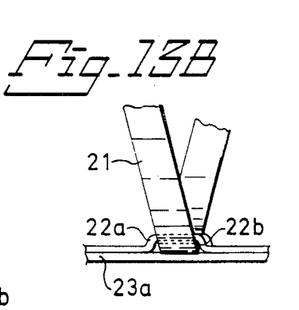

FIG. 15 shows in enlargement an embodiment of a guide member providing for good spring stability also at large expansion numbers. Guide member 27 is provided with a rectangular recess 28 for guiding a band-formed coil spring 29, as shown in cross section. The dimensions of recess 28 are suitably selected so that the coil spring member 29 can easily slide through the recess when the spring is expanded or contracted. At the same time it is prevented that the coil spring tilts so that the tilting forces are taken up by the guide member and the associated thread arranged in hole 25.

Figure 16:
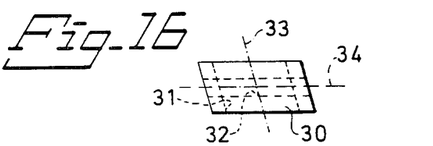
FIG. 16 shows the guide member according to FIG. 15 seen from above.

FIG. 16 shows a corresponding guide member 30 but seen from above. The dashed lines 31 indicate a recess of rectangular cross section, and the dashed lines 32 correspond to hole 25 of FIG. 15. As is clear from the figure the center lines 33 and 34, respectively, cross each other with an angle different from 90°. Hereby the guide member can be adjusted to the pitch angle of the coil spring in relation to the thread and in this manner the movement of the coil spring when changing the diameter of the spring will be facilitated.

Figure 17:
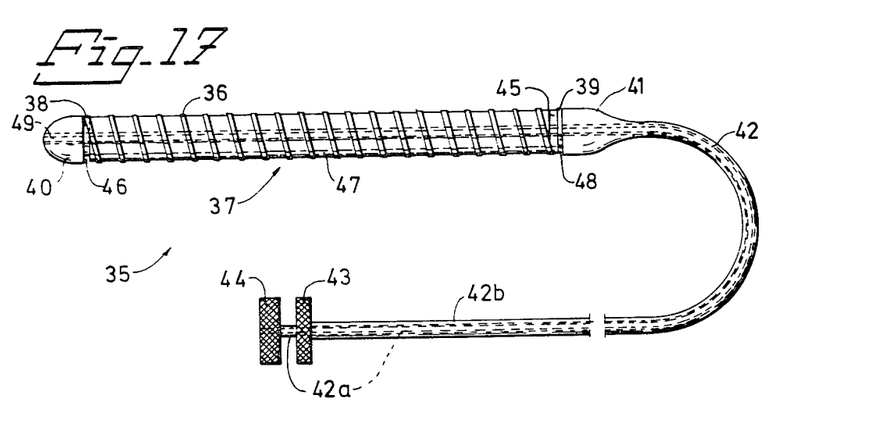
FIG. 17 shows diagrammatically an overall view of an embodiment of the device of the invention.

FIG. 17 shows an embodiment of the device according to the present invention in the form of an instrument 35 for performing surgical operations.

A coil spring 36 is in contracted state arranged about a cylindric carrier body 37. This body is provided with a tubular central part 47 and end sections 40, 41, which by a rotary ring 45 are rotatable relative to each other and also axially displaceable in relation to the central part 47. At one end of carrier body 37 a flexible coaxial cable 42 is connected to one end section 41. This coaxial cable 42 contains an outer tubular part 42*b* an inner element 42*a* concentrically arranged extending through end section 41 and the central part 47 of carrier body 37 all the way up to the second end section 40, to which it is securely attached.

At the free outer end of coaxial cable 42 there are arranged nob members 43, 44, of which one nob member 43 is connected to the outer part 42*b* of the coaxial cable, whereas the other nob member 44 is connected to the inner element 42*a* of the coaxial cable.

One end 38 of coil spring 36 can be clamped in a slit 46 arranged between the central part 47 of the carrier body and the end section 40 by the axial displacement of the latter. The other end 39 of coil spring 36 is in a corresponding manner clampable in a slit 48 between end section 41 and rotary ring 45, also this in view of the axial displacement of end section 41.

The clamping of ends 38, 39 of coil spring 36 in slits 46 and 48, respectively, as well as the release of the ends from the slits can be provided by axial displacement of the inner element 49 of the coaxial cable 42 by manoeuvring nob member 44 which also operates for providing the axial displacement. Rotating both ends 38, 39 of coil spring 36 in relation to each other in accordance with the principle illustrated in FIGS. 1–3 can be provided by rotating nob members 43, 44 relative to each other.

In the instrument shown in FIG. 17 a central through-going passage 49 is arranged by means of which contrast liquid, other instruments for medicinal investigation can be inserted into the blood vessel.

The function of the device shown is briefly as follows. In the state shown in FIG. 17, i.e. with coil spring 36 contracted, carrier body 37 with coil spring 36 attached in the respective slits 46, 48 is inserted through an easily accessible location on the blood vessel in question and fast on to the defective position of larger diameter. The expansion of coil spring 36 is provided by rotating nob means 43, 44 in relation to each other. After coil spring 36 has expanded to tension-less state or essentially tension-less state its ends 38, 39 are released by axial displacement of nob members 43, 44 relative to each other so as to widen slits 46, 48. In this manner ends 38, 39 of the coil spring 36 are released, whereafter coaxial cable 42 and support body 37 attached thereto can be removed from the blood vessel.

Figure 18:
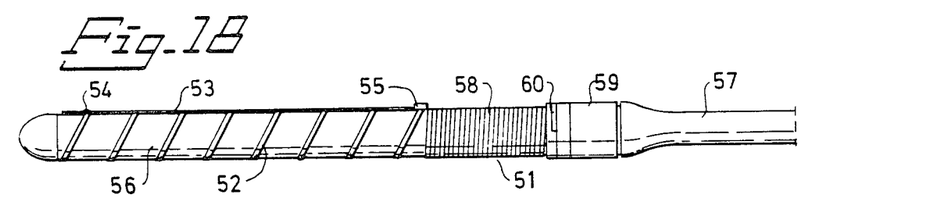
FIG. 18 shows in overall view an alternative embodiment of the device according to the present invention.

In FIG. 18 there is shown an alternative embodiment of the device according to the invention in the form of an instrument generally designated 51 for carrying out surgical operations. The device is based upon the spring principle in accordance with that shown in FIG. 5 and in connection to the embodiment shown in FIGS. 13A and 13B. In FIG. 18 spring 52 is shown in contracted state. The axially extending support means 53 of the spring is securely attached to one end 54 of spring 52, whereas the spring at its other end is movable through a guide member 55 arranged on support member 53. Spring 52 and support member 53 are attached to a cylindric elastic and hollow body 56 by means of latches not shown in the figure, one at each end of support means 53. The latches can be released from the ends of support member 53 by means of for example a wire for each extending within hollow body 56 and a coaxial cable 57 connected thereto and can in this manner be controlled from the outside.

Between coaxial cable 57 and the end 55 of support member 53 the spring is wound about carrier body 56 with relatively close windings 58. The end 62 of spring 52 adjacent to the coaxial cable is releasably connected to a sleeve 59. The sleeve surrounds the cylinder carrier body 56 and can be rotated and axially moved by means of a flexible tube which is concentrically arranged in the coaxial cable 57.

The expansion of spring 52 is provided by rotating sleeve 59, the spring excess stored adjacent to the sleeve expanding simultaneously with spring 52 moving through guide means 55. During the expansion the sleeve is slowly brought forward by the axial movement of the flexible tube.

The total length of spring 52 has been adjusted in advance so that when the expansion is interrupted by the surrounding inner walls of the blood vessel only a minor length of spring material is found outside guide member 55. When the surgeon has checked that the spring has taken its correct position spring 52 with carrier member 53 will be released by releasing the said latches and the attachment of end 60. If in connection to applying the instrument it is found that the selected spring length is not suitable but need to be changed this can be done by contracting the spring before releasing latches and the end 60 by rotating sleeve 59 in the opposite direction, whereupon the instrument can be removed and spring 52 be replaced by another spring of suitable total length.

The excess 58 of the spring which has been exteriorly wound about body 56 in close windings may, according to another embodiment of the invention, be interiorly stored in a sleeve and by means of suitable members be fed out from said sleeve through guide member 55 (FIG. 18). This embodiment is shown in FIGS. 19 and 20 in axial and radial section, respectively.

According to this embodiment a feed cylinder 63 is eccentrically mounted in a cylindric housing 61. In housing 61 cams 66 are cut to form an interior trapezoid thread 67. Feed cylinder 63 is exteriorly covered by a rubber layer 64.

Figure 19:
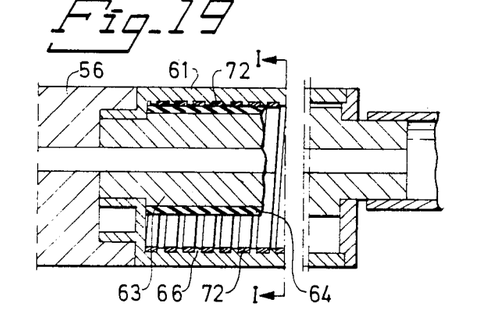
FIG. 19 shows enlarged a detail of an alternative embodiment of the device of FIG. 18.
Figure 20:
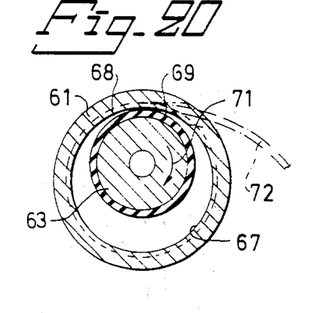
FIG. 20 shows the detail according to FIG. 19 in side view.

When using the device the band material 72 of the coil spring lies within trapezoid thread 67 and the rubber layer 64 arranged on the feed cylinder 63 is in pressing engagement against band material 72 along distance 68-69 (FIG. 20). If now feed cylinder 63 is rotated in the direction of arrow 71 spring band 72 will be advanced out through guide member 55 (FIG. 18) with simultaneous expansion of the spring. In view of the fact that feed cylinder 63 having rubber layer 64 engages interiorly along the whole length of trapezoid thread 67 the spring band 72 may be retracted back into housing 61 if feed cylinder 63 is rotated in the opposite direction, the coil spring being subjected to contraction.

The advantage of interior storage of excess of spring material in a casing in accordance with FIGS. 19 and 20 is significant. Thus, the contraction or expansion of the coil spring does not cause any disturbance or irritation of surrounding tissue in view of the fact that the spring excess is enclosed in a casing. Moreover, by means of the feeding arrangement and the guiding of the spring through a terminal guide member 55 (FIG. 18) a very even and controlled expansion of the spring along all of its length will be obtained. This latter fact means that the implantation of the spring will be significantly facilitated.

In certin cases it may be desirable to line the inner wall of a damaged blood vessel or other organ with e.g. porous artificial tissue, for example in order to obstruct a fracture in the blood vessel. Also such lining can be provided using the device according to the present invention.

Figure 21:
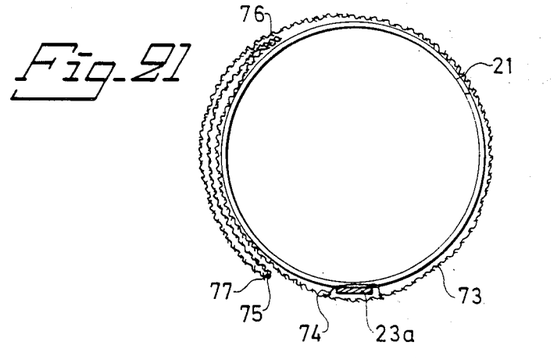
FIG. 21 shows a device according to the invention for the application of porous tissue.

FIG. 21 shows diagrammatically in a cross section a spring 21 in accordance with FIG. 13A in contracted state with support member 23A. A porous tissue in the form of a cylindric stocking 73 is arranged round the spring and attached to carrier member 23A by means of fine threads 24. The tissue is overlappingly folded double at folds 75 and 76 so as to closely enclose spring 21 in contracted state. Stocking 73 is held in this position by means of an axially extending thin metal wire 77 arranged in fold 75.

After spring 21 with surrounding stocking 73 has been inserted to the damaged site by means of an instrument, for example according to FIG. 17, metal wire 77 is removed whereupon spring 21 is brought to expand. During the expansion of spring 21 stocking 73 will be opened out and will, finally, be brought to firm engagement against the inner side of the damaged site of for example a blood vessel.

As an alternative to the embodiment described above the cylindrical stocking may, of course, be made of a stretchable material which, in connection to the expansion of the spring, can be stretched to an expanded state without using double folding of the material. Such material may for example be a round stitched or round knitted close meshed article, for example of the tricot type. Such alternative embodiment is, of course, particularly useful at lower expansion numbers, for example in such cases when the instrument with the spring in contracted state is inserted into a blood vessel of a relatively constant diameter but where nontheless certain contraction in relation to the inner diameter of the blood vessel is necessary in order to avoid damages to the inside of the blood vessel in connection with inserting the instrument into the vessel.

It should be observed that the present invention is not limited to the particular embodiments described above which only are intended to illustrate the invention. Thus, the housing described in FIGS. 19-20 instead of the eccentrically mounted feed cylinder 63 may contain any suitable feed means by which the spring can be moved out from and into casing 61. As conceivable alternatives there may be mentioned a concentrically arranged feed roller or a feed screw which is axially moved in connection with storing of the spring and thus after completed feeding of the spring will be rotated back into housing 61 before removal of the instrument from the site of application.

Moreover, the embodiment described in connection with FIGS. 13A and 13B using a fixed guide member at each end of the spring for simultaneous feeding at both ends of the spring, can be designed so that the spring at its mid point is firmly anchored to carry a member 23A. In this way two spring halves are formed, each half being associated with a casing or other storage means.

Figure 22:
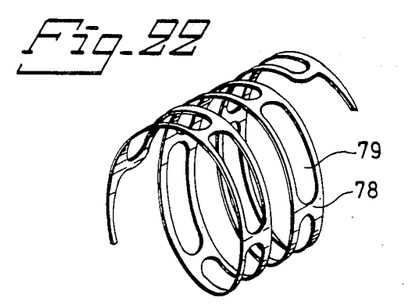
FIG. 22 shows an embodiment using a flat spring material with recesses.

In the embodiment shown in FIG. 22 the spring is made of a band-shaped material 78 which has been provided with elongated openings 79, for example by punching. In this manner the spring takes the shape of a ladder. Spring 78 which can be expanded in the same manner as the spring of FIG. 1 shows quite good stability and the risk for tilting of the spring in the manner shown in FIG. 10 has been eliminated. By suitable choice of band thickness and width of the step iron-like remaining parts of the band the good stability can be combined with high expansibility from a small diameter to a large one.

Figure 23:
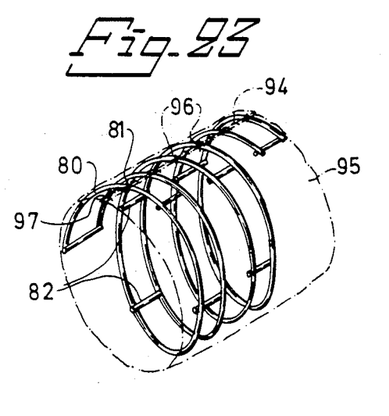
FIG. 23 shows an embodiment designed as a ladder-like double spring.

Springs possessing good stability similar to that of FIG. 22 can be manufactured in another manner than by punching openings. Thus, there is shown in FIG. 23 a ladder-like spring made from a round wire instead of from a flat band. In this case the spring has been manufactured by initially producing a ladder by attachment of two adjacent parallel wires 80 and 81 by means of transverse elements 82. This device may also be regarded to be a double spring composed of two single springs 80 and 81.

As previously mentioned, there is often a need to line the inner wall of a damaged organ with some tissue. In connection to FIG. 23 there is shown an arrangement whereby such tissue can be introduced into a damaged organ. Even if the arrangement illustrated in connection to the particular spring shown in FIG. 23 it should be noted that it is, of course, applicable to all types of coil springs.

The spring of FIG. 23 is surrounded by a stocking 95 of some porous material which, by means of stitches or the like indicated at 97, is attached to a longitudinally extending bar or rigid wire 94, which in turn is attached to spring 80, 81 at crossing points 96 in a suitable manner, for example by spot welding, gluing or the like.

By this arrangement the spring can act as a graft in implantation in for example a blood vessel, and thanks to the fixation of stocking 95 to the axially extending wire 94 it is kept in place during the whole application operation so that after application in the blood vessel it wholly surrounds spring 80, 81 thus forming an artificial tissue in the blood vessel.

Stocking 95 is suitably made of some stretchable porous material which can follow the spring material in the expansion of the spring in connection with the application at the intended location. Thus, it can consist of any knitted or stitched material of tricot type with a necessary stretchability or some type of crêpe product. The alternative is a stretchable plastic film, i.e. elastomer, for example of silicon resin.

Figure 24:
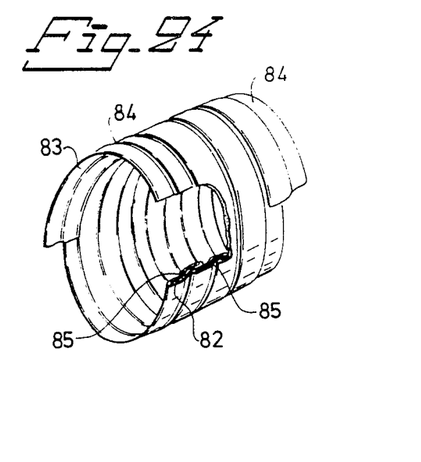
FIGS. 24 and 25 show an embodiment of the coil enabling overlapping between adjacent turns.

The embodiments of the springs shown in FIGS. 22 and 23 may as alternative to the embodiment just described be used as carriers for porous materials, for example tissue, which is illustrated in FIG. 24.

Figure 25:
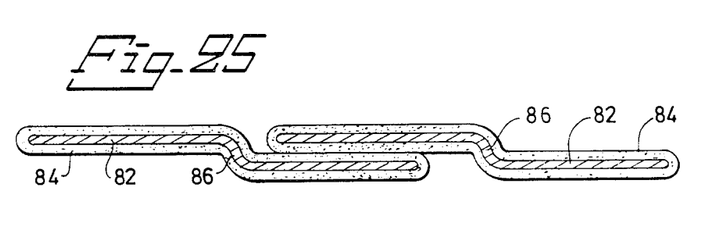

A ladder-like spring 83, designed for example like the spring of FIG. 22 or 23, is covered with porous material 84. In order to enable the desirable density between the spring turns the supporting double spring has, however, been somewhat modified in that the cross steps of the ladder, corresponding to elements 82 of FIG. 23, have been arranged in step position 85. In this manner the spring turns overlap each other and the desired density can be obtained. FIG. 25 shows in enlargement an axial section through two adjacent turns of the spring of FIG. 24. As is seen the cross elements 82 are provided with a shoulder 86. The spring is covered with porous tissue 84.

As is clear from FIGS. 24 and 25 sealing will be obtained even if the spring is subjected to axial movement. This is of importance if it is desirable for example to use the device according to FIG. 17 to expand the spring. Since the distance between members 38 and 39 is constant the pitch of the spring will be changed when these members are rotated relative to each other. By using the embodiment of FIGS. 24 and 25 this is made possible with maintained sealing in view of the fact that cross elements 82 slide in relation to each other in an axial direction. It is for example possible to design the spring according to FIG. 24 so that when it is in contracted state attached to the device according to FIG. 17 the overlap between the turns is relatively large whereas after the expansion the overlap is relatively small.

If it is desirable to maintain the same pitch in contracted as well as expanded state of a spring, according to for example FIGS. 24-25, this can be provided by modifying the device of FIG. 17 so that members 38 and 39 are subjected to axial movement towards each other or from each other when the spring is expanded and contracted, respectively. In this manner the pitch can be maintained relatively constant, which may be of advantage, particularly with regard to the embodiments according to FIGS. 22-25.

In some cases it can be suitable that the porous tissue, rather than being attached on the outside of the ladder-like devices, is designed in the form of semi-permeable sections of the band-like material. Thus, in this case openings 79 of FIG. 22 are replaced by a thinning of the band-material proper, in which thinning very fine perforations have been applied so that the same perforated surface will be obtained. Also in this case cross elements 78 form the necessary rigidification.

A further advantage of the device according to FIG. 24 is the fact that the porous material does not necessarily need to be elastic in order to participate in the expansion of the spring.

Figure 26:
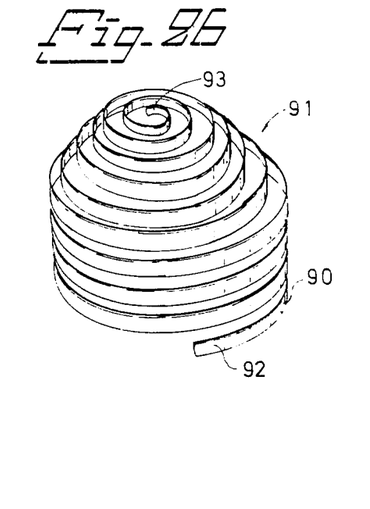
FIG. 26 shows a modified embodiment of the spring of the device, the spring providing for filtering function.

FIG. 26 shows a modified design of the spring in the device according to the invention. The modified spring shown in the figure generally indicated 90 is across the major part of its length designed as a conventional spring of constant diameter, whereas at the upper end 91 as shown in FIG. 26 it is designed with a diminishing diameter so that the spring 90 in unloaded state has the configuration shown in the figure. In order to facilitate the following description of the function of the spring the lower free end of the spring has been designated 92 whereas its free upper end has been designated 93.

In regard to contraction or expansion of spring 90 in connection with application at the intended location the function of the spring shown in FIG. 26 is the same as that of the previously described embodiments of the spring. However, in view of the fact that spring 90 is provided with a diminishing end 91 certain modification of the instrument to be used for operating the spring may be desirable. For example the instrument shown in FIG. 17 can be modified for adaptation to the spring according to FIG. 26 by excluding end section 40 and providing the inner element 42a at the end extending through carrier body 37 with a cross groove intended to accomodate and hold the upper free end 93 of spring 90. The other end 92 of spring 90 may then in the same manner as described in connection to FIG. 17 be held at the other end of carrier body 37 in connection to end section 41, whereupon in the manner previously described spring 90 can be contracted by rotating rotary members 43, 44 in relation to each other.

With spring 90 in contracted state it may thus be applied to the desired location within a blood vessel, for example Vena Cava Inferior for the purpose of preventing lung embolia. Previously known filter means intended for application within blood vessels for the purpose of entrapping tromboses are subject to the disadvantage that they are permanently attached in the blood vessel by points or hooks or the like whereby correction of location or removal of the filter is not possible. Example of such a device is described in U.S. Pat. No. 3,540,431.

By using the device according to the present invention such as that illustrated in FIG. 23 these drawbacks are, however, avoided while obtaining essential advantages, among which the following may be mentioned:
1. the spring with filter function is self-attaching by engagement against the inner wall of the vessel without causing damages to the inner wall;
2. the position of the spring can be corrected and removal of same is possible;
3. the device results only in an insignificant reduction of the flow across the section of the blood vessel;

4. the application of the device is significantly simpler than that of the prior art.

In order to prevent clogging of the diminishing end 91 of spring 90 by small lumps of coagulated blood a suitable distance between the spring turns in the diminishing part of the spring is about 3 mm. By using such distance the passage of larger tromboses is avoided whereas too early clogging of the diminishing part of the spring is avoided.

In connection to the embodiment of FIG. 26 and also in connection to other embodiments of the spring of the device of the present invention a spring inserted and applied in for example a blood vessel can be removed in the following manner. A flexible tube of a diameter adjusted to the blood vessel is inserted up to the end 92 of spring 90 or further up to its other end 93, whereupon the spring end is grabbed in a suitable manner by means of a grip member, whereupon the spring can be retracted through the tube without damaging the surrounding tissue. This procedure can be suitable to resort to in case the spring has taken a wrong position or has come to a wrong location in the blood vessel.

Figure 27:
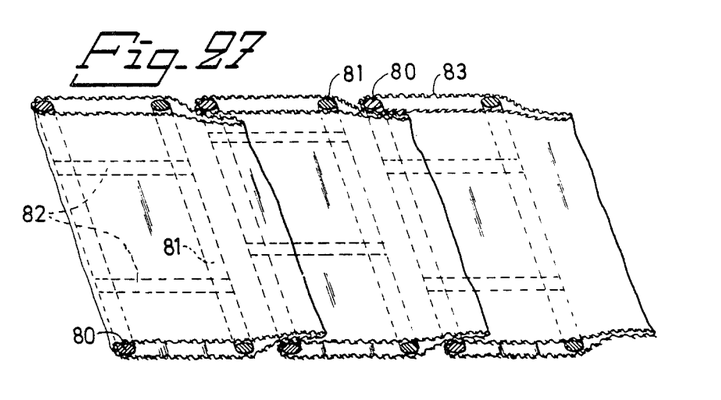
FIG. 27 shows an alternative embodiment where the spring has been covered with porous tissue.

FIG. 27 shows an embodiment modified in relation to the device according to FIGS. 24 and 25, whereby the inner wall of a damaged organ can be lined with porous tissue. The embodiment contains springs of the type illustrated in FIGS. 22 and 23 and reference numerals of the figure contain the corresponding designations as FIG. 23. According to FIG. 27 the double spring 80-82 is covered with stocking 83 of porous tissue surrounding the separate turns in the spring along the whole length of the spring period. The stocking 83 extends side-wise outside the spring material whereby there is provided overlap inside adjacent turns of the spring, as is clear from FIG. 27. Also in this case there is obtained sealing if the spring is moved in an axial direction, for example if the device according to FIG. 17 is used to expand the spring.

In other respects the device according to the invention contains the following features taken each per se or in any combination, namely:

(a) that said other state (FIG. 2; 4) essentially corresponds to unloaded condition of the coil spring 1; 36;

(b) that shaft 42a and sleeve 42b are releasably connected to coil spring 36;

(c) an axially extending guide bar 23 arranged at the periphery of the spring on which at least one guide member is displaceably arranged and through which the spring material can move tangentially in connection with the contraction or expansion of the spring;

(d) fixed guide members 22 distributed over the said given length of the spring and arranged at the periphery of the spring on an axially extending support member 23, the spring material 21 moving tangentially through said fixed guide members in connection with the expansion or contraction of the spring;

(e) that the end sections or parts thereof 40, 41 of the carrier body 37 are axially displaceable relative to the central part 47 so that in the gaps 46, 48 between the central part 47 and the respective end sections 40, 41 the ends 38, 39 of the spring can be releasably attached;

(f) that at least one section or part thereof 40, 41 is axially displaceable by means of a member 44 arranged at the free end of the coaxial cable 42;

(g) an axially extending support member 23a at the circumference of the spring 21 at one end 21a of which the spring 21 is attached and at the other end 21b of which there is provided a fixed guide member 22a through which the spring material can move in connection with a contraction or expansion of the spring 21;

(h) an axially extending support member arranged at the periphery of the spring at both ends of which there are arranged fixed guide means through which the material of the spring can move in connection with the contractional expansion of the spring;

(i) an elongated carrier body 56 about which the spring 52 is arranged, a cassette magazine arranged at one end of the carrier body including a cylindric cassette housing 61, a feed member 63 rotatably arranged therein by which the spring can be moved for contraction or expansion by rotating feed member 63 in one direction or the other;

(j) that the feed member consists of a feed cylinder 63 eccentrically mounted in the cassette housing 61 a cylinder 63 at its periphery engaging the inside of the cassette housing 61;

(k) a trapezoid thread provided on the inside of cassette housing 61 in which the spring 52 can glide;

(l) that feed cylinder 63 on its exterior is provided with a friction coating 64 of for example rubber or plastic;

(m) an elongated carrier body 56 about which the spring 52 is arranged and at one end of which one end of the spring is releasably attached, a magazine section 58 extending from the other end of carrier body surrounded by the spring carrying at its outer end a rotary sleeve 59 to which the other end of the spring is releasably attached, and means for rotating and axially displacing rotary sleeve 59 relative to the carrier body 56;

(n) that stocking 73 by stretchability in the tissue is adaptable to the spring diameter in connection with the expansion of the spring;

(o) that stocking 73 by overlapping folding 75, 76 is adaptable to the spring diameter in connection with the expansion of the spring;

(p) that stocking 73 is attached relative to spring 21, for example by thread stitches.

In the instant disclosure the term "coil spring" refers to a helical spring of the traditional type. However, the spring used in the device of the invention need not necessarily have constant diameter or a constant pitch. The general configuration, however, is that of a helix.

The invention is also useful in certain kidney disorders, where so-called haemodialysis takes place. In this operation a needle or cannula is applied to the patient's arm so that blood is extracted from the body and after purification in a dialyser returned to the body. Since dialyses have to be repeated at least once a week problems arise in regard to the blood vessels of the patient. The problem has been solved by arranging a so-called by-pass providing a permanent connection between an artery and a vein, for example in the arm of the patient. This connection may be made of for example vessel prostheses or a vein taken from calves, so-called "solkograft". The advantage of using such a by-pass is the fact that the high pressure from the artery provides for expansion of the connecting vein making it easily accessible when inserting the cannula. Moreover, a large number of dialyses can be made before exchanging the connection. The connecting conduit is usually positioned beneath the skin and is attached to the artery and the vein by stitching.

However, also the connections hitherto used result in certain problems. When the prosthesis is withdrawn beneath the skin in an operation it may be folded and blocked. After the removal of the haemodialysis cannula the connecting prosthesis must be compressed to prevent too large a loss of blood. The artificial vein may then easily collapse resulting in subsequent impaired circulation. It has also been found that so-called stenoses, i.e. contractions, will be formed where the connection is attached to the vein.

It has now been found that the disadvantages associated with the above connecting conduits or prostheses can be eliminated by using the device of the invention by using the following procedure.

A helical spring of suitable diameter and of a suitable number of turns is attached in an instrument in accordance with the invention, for example as illustrated in FIG. 17, i.e. the spring is in contracted state.

A prosthesis, for example a solkograft, is attached at one end thereof to a vein of the patient by a few stitches. Then the device of the invention including the spring is inserted into the graft so that the outer end of the device with the corresponding end of the spring will reach a position about 2 cm inside the vein. Then the spring is expanded inside the prosthesis and released from the instrument which is then withdrawn from the prosthesis.

By means of a cut beneath the skin the free end of the graft is transferred up to the opening of the artery and attached thereat.

The arrangement described above has been found to result in great advantages.
1. The graft will not collapse when implanted due to the action of the spring.
2. The connecting conduit or prosthesis may safely be compressed or clamped after removal of the cannula for reducing blood losses. The conduit immediately returns to full diameter in view of the action of the spring.
3. It is easy to find the prosthesis under the skin and this in turn facilitates puncturing the conduit.
4. It has been found that the risk for the formation of stenoses in the vein is reduced. In using the conventional technique the site of connection must be changed and moved to another location at least once a year due to formation of stenosis.

In addition to the application of the invention as described above there are also other important areas where the device of the invention may be used. Thus, there are presently difficulties in performing animal tests, for example on dogs, where it is desirable to introduce for example drugs several times a day to study the effects in long-time tests. Up to now such experiments have not been feasible inter alia in view of the fact that animals are subject to rapid formation of stenoses.

By using the arrangement described above tests of lengthy duration can be made on for example dogs with one single permanent connection.

We claim:

1. A device of the type including a helically shaped spring of a predetermined length and pitch provided with first and second ends and means for expanding the spring from a first state of a certain diameter to a second state of a larger diameter and vice versa, the improvement comprising: an arrangement of said expanding means to rotate the ends of the spring relative to each other solely by means of mechanical actuation of said expanding means so as to maintain said predetermined length of the spring, transition from said first state to said second state effected by reduction of a number of spring turns in the length of the spring with a simultaneous increase in the pitch of the spring.

2. A device according to claim 1, wherein said spring is connected to an additional section of spring material at one of said ends of the spring, said additional section of spring material provided with a different pitch than said spring, so that said transition from said first state to said second state takes place independent of said pitch and said number of spring turns.

3. Device according to claim 1, characterized thereby that one end (38) of the spring (36) is attached to a shaft (42a) which is centrally arranged inside the spring, whereas its other end (39) is connected to a sleeve (42b) surrounding the shaft (42a), whereby through rotation of the shaft and/or the sleeve relative to each other reduction or increase of the diameter of the spring (36) is provided.

4. Device according to claim 1, characterized thereby that the spring material (29) as seen in axial cross section has a radially flattened shape to reduce the risk for spring collapse.

5. Device according to claim 4, characterized thereby that the transverse sections or cross members (82) are provided with a centrally positioned radially oriented shoulder (85, 86) whereby adjacent spring turns can overlap.

6. Device according to claim 5, characterized by a stocking (84) of porous tissue surrounding the individual turns of the spiral (78; 80–82) in substantially the whole length of the spiral material.

7. Device according to claim 1, characterized by a stocking (73) of stretchable tissue surrounding the spring intended for implantation together with the spring.

8. Device according to claim 1, characterized thereby that the spring material (78) is provided with radial through-recesses (79) between which axial and transverse minor sections remain, whereby the expansive or contractional capacity of the spring will be increased.

9. Device according to claim 1, characterized thereby that the spring is composed of a co-extensive double spiral or spring wherein the spiral elements (80, 81) are connected by means of tangentially distributed and axially extending cross members (82).

10. Device according to claim 9, characterized by a stocking (83) of porous tissue surrounding the individual turns (80, 81) of the spiral in the whole length of the spiral material and extending laterally outside the spiral material thereby providing overlap within the adjacent turns of the spiral.

11. Device according to claim 1, characterized thereby that the spring (90) is designed to act as a filter after application by having at at least one end (91) thereof a diminishing diameter.

12. Device according to claim 11, characterized thereby that the distance between the turns of the diminishing end (91) of the spring (90) defining the flow passage is about 3 mm.

13. Device according to claim 1, characterized by an axially extending and elongated member (94) coextensive with the periphery of the spring which is attached to the spring at one location (96), and by a stretchable stocking (95) of porous material surrounding the spring which is attached to said member (94) and which is intended to be implanted together with the spring.

14. Device according to claim 1, characterized by a cylindrical tubular carrier body (37) arranged within the coil spring (36) comprising a central part (47) and being provided with end sections (40, 41) at the ends (38, 39) of the spring rotatable relative to each other, the ends (38, 39) of the spring (36) being connected to the respective end sections (40, 41), and means (42, 43, 44) with the help of which the said end sections (40, 41) can be rotated relative to each other to expand or to contract the spring (36).

15. Device according to claim 14, characterized in that said means comprise coaxial members (42) connected to the one end section (41), the interior element (42a) of the said members extending through the carrier body (37) and being at the end connected to the other end section (40), rotators (43, 44) being arranged at the outer free end of the coaxial members.

16. A device according to claim 1, wherein the spring is maintained at substantially constant temperature when the ends are rotated.

17. A method for transluminal implantation of an intravascular prosthesis, said prosthesis comprising a helically shaped spring in a contracted state with a predetermined length and pitch provided with first and second ends and means for expanding the spring from a first state of a certain diameter to a second state of a large diameter and vice versa, the method including the steps of:

rotating the ends of the spring by said means for expanding the spring, maintaining the predetermined length of the spring during said rotation, reducing the number of spring turns while rotating said spring, and effecting a simultaneous increase in the pitch of the spring solely by means of mechanical actuation.

18. A method according to claim 17 including the step of selecting a spring of a diameter in unloaded state somewhat larger than the internal diameter of the vessel at said other location so as to provide for an internal pressure of the spring against the inner walls of the vessel.

19. A spring of the type comprising a predetermined length of helical spirals provided with a predetermined width and defined by a predetermined pitch and provided with first and second ends, said helically shaped spirals defining openings circumferentially spaced along the length of the spring, said openings defined within said predetermined width and spaced in an interrupted pattern along said predetermined length, said interruption provided by axially extending sections of the spring.

* * * * *